United States Patent [19]

Mann

[11] 4,333,331
[45] Jun. 8, 1982

[54] CALIBRATING UNIT FOR CALIBRATING A HYDRAULIC OR ELECTRIC PRESSURE GAUGE, ESPECIALLY OF A PROBING DEVICE

[75] Inventor: Adriaan B. Mann, Delft, Netherlands

[73] Assignee: Goudsche Machinefabriek B.V., Gouda, Netherlands

[21] Appl. No.: 177,771

[22] Filed: Aug. 13, 1980

[30] Foreign Application Priority Data

Aug. 17, 1979 [NL] Netherlands .................... 7906279

[51] Int. Cl.³ ............................................. G01L 27/00
[52] U.S. Cl. ................................................... 73/4 R
[58] Field of Search ........................... 73/4 R, 84, 4 D

[56] References Cited

FOREIGN PATENT DOCUMENTS 556195  9/1943  United Kingdom ................. 73/4 R Primary Examiner—Donald O. Woodiel

[57] ABSTRACT

A calibrating unit for calibrating a pressure gauge includes a piston (7) which may be loaded by pressurized oil and which may be fastened at its upper end to the pressure gauge. A pressure piece (11) being movable within the piston (7) can be loaded at its upper side by a measuring member (3) of the pressure gauge and can transmit this load at its lower side to a spring system (15,16,17) resting on the housing (6) of the unit. The movement of the pressure piece (11) is determined by a measuring instrument such as a measuring watch (21). The deflection of the pointer of this watch is a calibrating measure for the pressure gauge.

6 Claims, 1 Drawing Figure

U.S. Patent Jun. 8, 1982 4,333,331
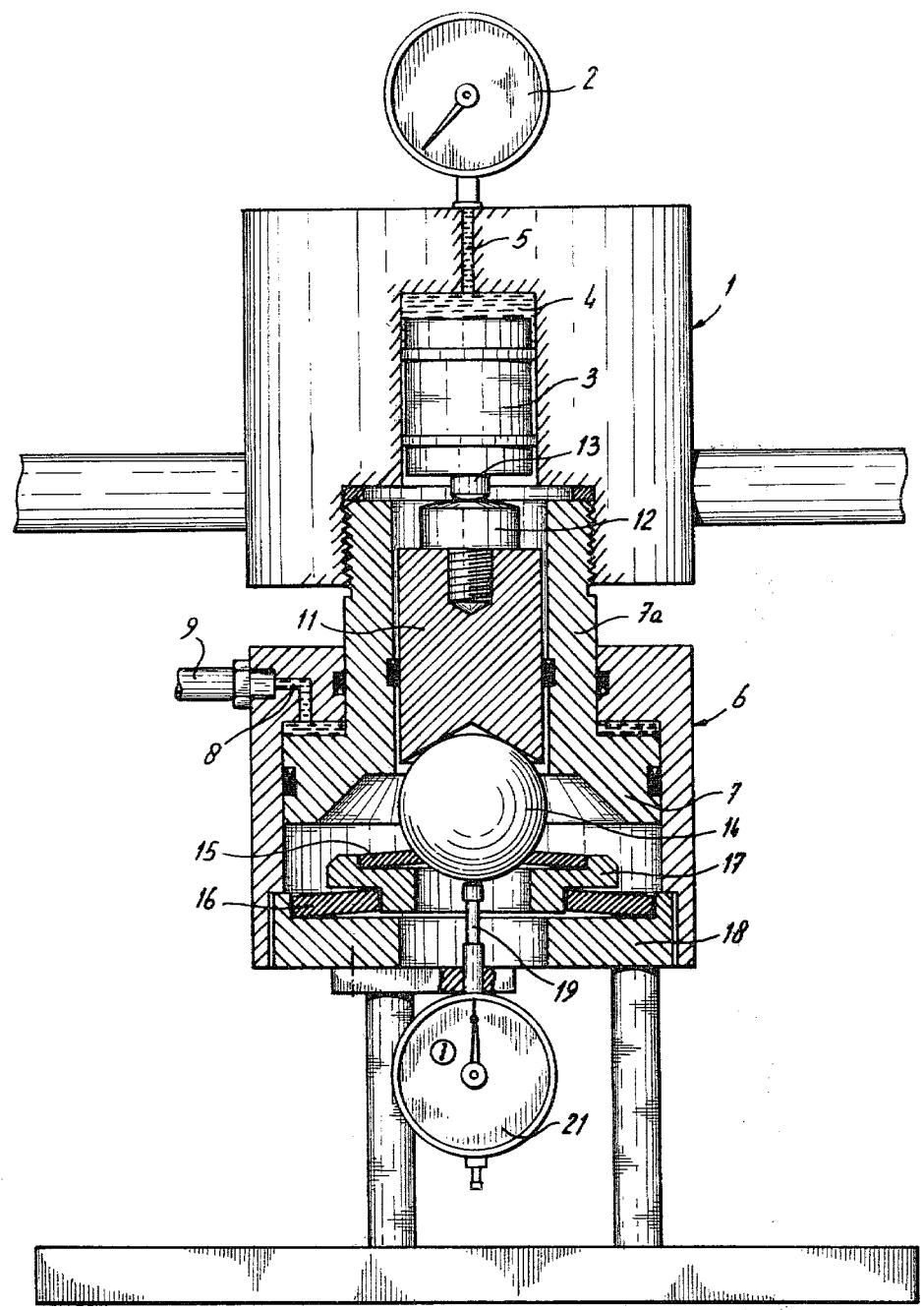

CALIBRATING UNIT FOR CALIBRATING A HYDRAULIC OR ELECTRIC PRESSURE GAUGE, ESPECIALLY OF A PROBING DEVICE

The invention relates to a calibrating unit for calibrating a hydraulic or electric pressure gauge, especially of a probing device.

A probing device is used for forcing a cone connected to the lower end of a string of probing pipes and eventually an additional friction sleeve into the ground. The cone may be loaded separately by means of an internal bar. In case of an additional friction sleeve between the cone and the coupling member, the combination of friction sleeve and cone may also be loaded after slidingly extending the cone. The probing device comprises a manometer with which the hydraulic pressure can be measured, the measured value being a measure for the cone resistance, the local adhesive hold and the total adhesive hold. These values can be used to calculate foundations. Based on the correlation between the cone resistance and the local adhesive hold the kind of soil may be determined. The measurement of the manometer is rather inaccurate. This implies that upon calculating the load capacity of a fundation piller or a bed plate, the settling of a foundation and the like, a large safety factor has to be introduced. The foundation will have to be relatively heavy. More accurate measurements may be made by substituting the hydraulic measurement with the aid of a manometer by a electric measurement for instance with the aid of strain gauges or an inductive measuring system. Between the measuring system and the recording apparatus there will be a cable running through a slot of a pressure piece engaging the upper end of the upper tube and loaded by a pressure cylinder.

It is important that the hydraulic or electric pressure gauge indicates the right value of the pressure. Calibrating is often required. It is known to make use of a complicate electronic equipment for calibrating. This equipment is expensive, vulnerable and it is difficult to adapt it to different measurement ranges.

The most important object of the invention is to avoid these disadvantages and to provide a calibrating unit to the type indicated in the preamble, said unit having a simple sturdy construction and is universally applicable and may be easily adaptable to different measuring ranges.

According to the invention the calibrating unit comprises at least one housing, a piston within that housing and having a connecting porting protuding from the upper side of the housing to connect the piston with the casing of the pressure gauge to be calibrated, a feeding channel in the wall of the housing meant for the supply of hydraulic liquid to load the piston, a pressure piece movable within the piston and being able to be loaded at its upper side by a measuring member of the pressure gauge to be calibrated said pressure piece being able to load a spring element mounted underneath the pressure piece and resting on the housing, and a measuring watch or such like for determining the movement of the pressure piece.

In the use the piston is connected with the housing of the pressure gauge to be calibrated, after which hydraulic liquid having an increasing pressure is led to the housing. The piston is loaded with respect to the housing of the calibrating unit and is moved, the casing of the pressure gauge to be calibrated being taking along. This movement is passed to the pressure piece through the measuring member (for instance a measuring plunger) of the pressure gauge to be calibrated and the pressure is passed to the spring element resting on the housing through this pressure piece. Consequently the system of forces forms a closed circuit. The movement of the pressure piece is determined by the measuring watch. The relation between the deflection of the measuring watch and the load is known (dependent on the spring characteristics of the spring element). This deflection is a measure for the force exerted on the casing of the pressure gauge to be calibrated.

The force on the casing of the pressure gauge following from the deflection of the measuring watch can be compared with the value of the force read on the pressure gauge itself.

An adaption to different measuring ranges can be obtained by employing spring elements to different characteristics.

An excellent transmission of the force from the pressure piece to the spring element is obtained when between the conical lower face of the pressure piece and the spring element a ball is mounted on which a pin of the measuring watch engages.

Preferably the spring element comprises one or more Belleville springs, said springs being supported in an easily exchangable way on a bottom plate of the housing.

To make the pressure piece suitable for loading by the measuring plunger of a hydraulic pressure gauge as well as for loading by a measuring cone of an electric pressure gauge, an exchangable intermediate piece may be mounted on the upper side of the pressure piece.

In case of an hydraulic pressure gauge the upper face of the intermediate piece is convex, while in case of an electric pressure gauge the upper face of the intermediate piece comprises a conical recess.

The invention will now be elucidated with the aid of the FIGURE showing a cross-section of a calibrating unit connected to a hydraulic pressure gauge of a probing device.

The calibrating unit shown is meant to calibrate the manometer of a hydraulic pressure gauge of a probing device for determining the so-called cone resistance, local adhesive hold and total adhesive hold.

The casing of the pressure gauge to be calibrated is indicated by 1, the manometer by 2. The measuring plunger 3 may pass a load to the manometer 2 via the oil in chamber 4 and channel 5.

The calibrating unit comprises a housing 6 having a piston 7 movable therein said piston being provided with a connection portion 7a protuding from the housing 6 and fixed by screwing to the casing 1 of the pressure gauge to be calibrated.

An oil conduit 9 is connected with a channel 8 in the housing 6.

Within the piston 7, 7a a cylindrical pressure piece 11 is movable. A hardened intermediate piece 12 is mounted on the upper side of the pressure piece 11. A pin 13 of the measuring plunger 3 of the pressure gauge to be calibrated engages the convex upper face of this intermediate piece 12.

The conically recessed lower face of the pressure piece 11 rests on a ball 14 which on its turn rests on a spring element comprising two Belleville springs 15,16 and an intermediate centring ring 17.

This spring element rests on an easily removable bottom plate 18 of the housing 6. The pin 19 of a measuring watch 21 engages the lower portion of the ball 14. Each movement of the pin is converted into a deflection of the pointer of the measuring watch 21.

Sealing rings are mounted between the housing 6 and the pistion 7 while between the portion 7a and the pressure piece 11 a centring ring is placed.

The calibrating unit functions as follows:

After the connecting portion 7a is fixed by screwing to the casing of the pressure gaunge to be calibrated, oil is pumped through conduit 9 and channel 8 into the space between the housing 6 of the calibrating unit and the piston 7. The load on the piston is transmitted in the above-mentioned way to the bottom plate 18 of the housing 6 through the casing 1, the oil in chamber 4, the measuring plunger 3, the pin 13, the intermediate piece 12, the pressure piece 11, the ball 14 and the spring element 15, 16, 17. The deflection of the measuring watch 21 has a functional relation with the deflection of the manometer by means of the spring characteristic of the spring element; consequently this deflection forms a calibrating measure for the manometer.

To enable calibrating in another measuring range (for instance the measuring range between 100 and 200 kN instead of the measuring range between 5 and 50 kN) the spring element can be replaced. In case of a screw connection between the bottom plate 18 and the housing 6 this replacement can be carried out in a short time. The calibrating unit can be made suitable for calibrating an electric pressure gauge. Therefore only the intermediate piece 12 having a convex upper face must be replaced by an intermediate piece having a cone shaped recess.

Within the scope of the claims several modifications are possible. Essential for the invention is that the load generated by the oil pressure and causing a deflection of the manometer 2 or the electrical indicator of the pressure gauge to be calibrated as well as a deflection of the measuring watch 21. is led back to the housing of the calibrating unit. The pressure piece 11 can be a portion of the measuring plunger 3.

I claim:

1. Calibrating unit for calibrating a hydraulic or electric pressure gauge especially of a probing device, wherein the calibrating unit comprises at least a housing having a wall, and upper side, and a bottom plate, a piston mounted within said housing and having a connecting portion protruding from the upper side of the housing for connecting the piston with a casing of the pressure gauge to be calibrated, a supply channel in the wall of the housing for supplying hydraulic liquid to load the piston, a pressure piece movable within the piston and having an upper side, a lower side and a lower face, said pressure piece being able to be loaded at its upper side by a measuring member of the pressure gauge to be calibrated and to load at its lower side a spring element resting on the housing, and a measuring watch or the like for determining the movement of the pressure piece.

2. Calibrating unit according to claim 1, wherein a ball is mounted between a conical recess in the lower face of the pressure piece and the spring element, a pin of the measuring watch engaging said ball.

3. Calibrating unit according to claim 1 or 2, wherein the spring element comprises at least one Belleville spring resting on the bottom plate (18) of the housing so as to be easily exchangeable.

4. Calibrating unit according to claim 1 or 2, wherein on the upper side of the pressure piece an exchangeable intermediate piece having an upper face, is mounted.

5. Calibrating unit according to claim 4, wherein the upper face of the intermediate piece is convex.

6. Calibrating unit according to claim 4, wherein a conical recess is made in the upper face of the intermediate piece.

* * * * *